US010245412B2

(12) United States Patent
Shimizu et al.

(10) Patent No.: US 10,245,412 B2
(45) Date of Patent: Apr. 2, 2019

(54) CATHETER

(71) Applicant: ASAHI INTECC CO., LTD., Seto-shi, Aichi (JP)

(72) Inventors: Hirotomo Shimizu, Nagoya (JP); Masatomo Ishikawa, Seto (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 0 days.

(21) Appl. No.: 15/140,646

(22) Filed: Apr. 28, 2016

(65) Prior Publication Data
US 2017/0113018 A1    Apr. 27, 2017

(30) Foreign Application Priority Data

Oct. 27, 2015    (JP) ................................. 2015-210511

(51) Int. Cl.
*A61M 25/00*    (2006.01)
(52) U.S. Cl.
CPC ...... *A61M 25/0052* (2013.01); *A61M 25/005* (2013.01); *A61M 25/008* (2013.01); *A61M 2025/0047* (2013.01)
(58) Field of Classification Search
CPC ............ A61M 25/0052; A61M 25/005; A61M 25/0068; A61M 25/10; A61M 2025/1093
See application file for complete search history.

(56) References Cited

U.S. PATENT DOCUMENTS

| 2004/0167496 | A1* | 8/2004 | Poole ...................... A61L 29/18 |
| | | | 604/529 |
| 2009/0171156 | A1* | 7/2009 | Yamaya ............. A61B 1/00082 |
| | | | 600/116 |
| 2010/0004593 | A1* | 1/2010 | Gregorich ......... A61M 25/0012 |
| | | | 604/96.01 |
| 2010/0094258 | A1* | 4/2010 | Shimogami ......... A61M 25/005 |
| | | | 604/527 |
| 2013/0018318 | A1 | 1/2013 | Ravichandran et al. |
| 2014/0214006 | A1* | 7/2014 | Hiroshige ......... A61M 25/0012 |
| | | | 604/527 |

FOREIGN PATENT DOCUMENTS

| DE | 38 12 188 C1 | 5/1989 |
| EP | 2174685 A1 | 4/2010 |
| JP | 2010-88833 A | 4/2010 |
| JP | 2010-527702 A | 8/2010 |

(Continued)

OTHER PUBLICATIONS

Mar. 27, 2017 Search Report issued in European Patent Application No. 16178436.8.

(Continued)

*Primary Examiner* — Lauren P Farrar
(74) *Attorney, Agent, or Firm* — Oliff PLC

(57) ABSTRACT

A catheter includes a catheter body having a lumen and a resin front end tip having a lumen that is in communication with the lumen of the catheter body and that is attached to the front/distal end of the catheter body. The catheter body and front end tip further include a coil body and/or a braid such that the coil body and/or braid are arranged along the lumen. Additionally, the catheter further includes a reinforcement body covering the coil body and/or the braid in the front end tip.

10 Claims, 7 Drawing Sheets

(56) References Cited

FOREIGN PATENT DOCUMENTS

| JP | 2012-249812 A | 12/2012 |
| JP | 2014-188337 A | 10/2014 |
| WO | 2007/067324 A1 | 6/2007 |
| WO | 2008/144587 A2 | 11/2008 |

OTHER PUBLICATIONS

Jun. 5, 2018 Office Action issued in Japanese Patent Application No. 2015-210511.
Dec. 4, 2018 Office Action issued in Japanese Patent Application No. 2015-210511.
Jan. 3, 2019 European Search Report issued in European Patent Application No. 18195848.9.

\* cited by examiner

CATHETER

CROSS REFERENCE TO RELATED APPLICATION

This application claims priority to Japanese Patent Application No. 2015-210511 filed in the Japan Patent Office on Oct. 27, 2015, the entire contents of which are incorporated by reference.

TECHNICAL FIELD

The disclosed embodiments relate to a catheter to be inserted into a tubular organ in a human body, such as a blood vessel, a gastrointestinal tract, and a ureter, as well as into a body tissue.

BACKGROUND

It is known in the art for catheters that are to be inserted into a tubular organ in a human body, such as a blood vessel, a gastrointestinal tract, and a ureter, as well as into a body tissue, to comprise a braid that includes two or more metal element wires. For example, Patent Document 1 (Japanese Patent Application Laid-Open No. 2014-188337) describes a catheter comprising a tubular body, a front end tip attached to the front end of the tubular body, and a reinforcement wire arranged inside the tubular body and the front end tip.

In the catheter of Patent Document 1, the stiffness of the catheter is enhanced due to a braid arranged inside the tubular body (hereinafter referred to as the "catheter body") and the front end tip. The braid prevents an inner cavity of the catheter from collapsing. Furthermore, replacing the braid with a coil body increases the torque transmissibility of the catheter from a base end of the catheter to a front end of the catheter.

SUMMARY

However, in conventional catheters, such as the catheter of Patent Document 1, even though the braid is arranged inside the catheter body and the front end tip, the front end tip may become detached from the catheter body during procedures. Thus, the front end tip may be inadvertently left inside the patient's body.

The disclosed embodiments include a catheter that reduces the occurrence of the front end tip being left inside the patient's body by preventing the front end tip from being detached from the catheter body.

The disclosed embodiments include a catheter comprising a catheter body and a resin front end tip. The catheter body has a distal end and a proximal end and forms a lumen. The resin front end tip has a lumen in communication with the lumen of the catheter body, and the front end tip is attached to the distal end of the catheter body. A wound body is disposed in the catheter body and in the front end tip such that the wound body extends along the lumen of the catheter body. The wound body is a coil and/or a braid. Additionally, a reinforcement body is disposed at least partly within the front end tip such that the reinforcement body radially covers the wound body.

According to the embodiments of the present disclosure, the front end tip may be prevented from being detached from the catheter body. Such may prevent the front end tip from being inadvertently left in the patient's body.

DETAILED DESCRIPTION OF EMBODIMENTS

Figure 1:
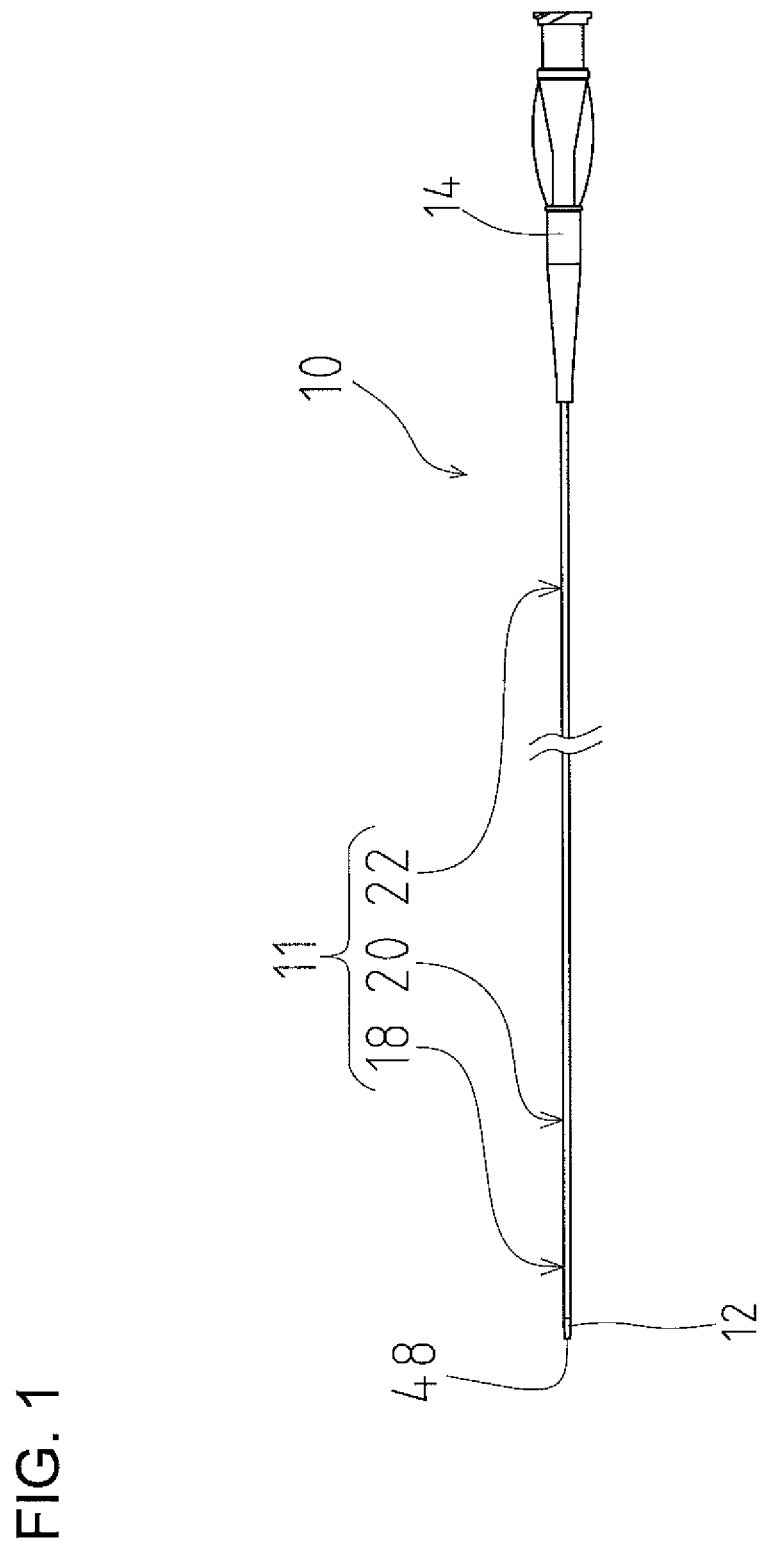
FIG. 1 shows a front view illustrating a catheter according to embodiments.
Figure 2:
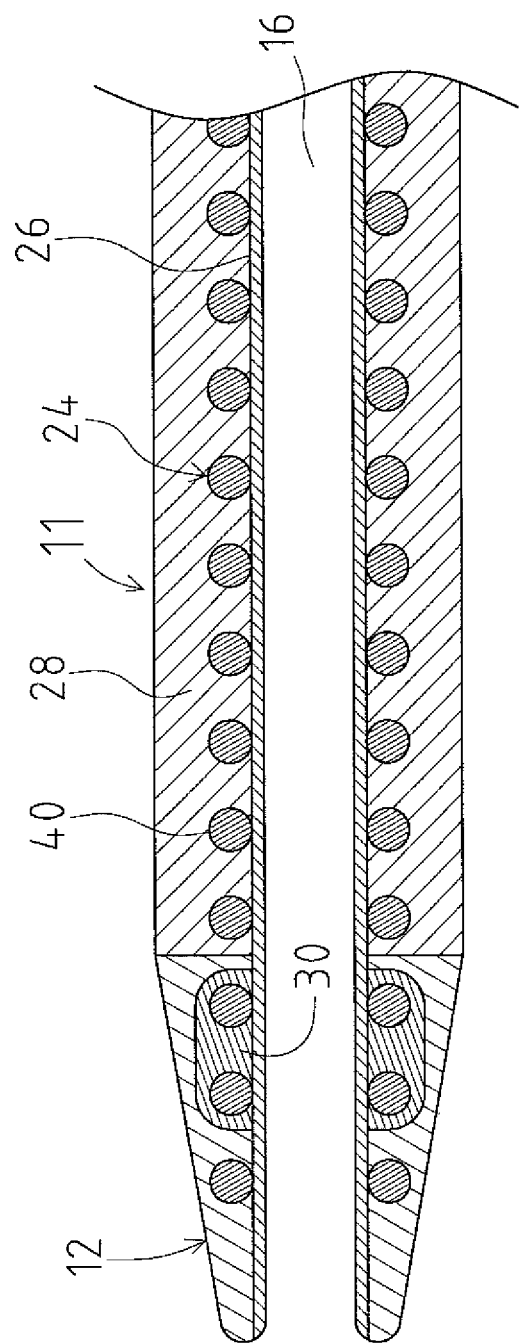
FIG. 2 shows a partial cross sectional view of the catheter according to embodiments.

FIG. 1 shows a front view illustrating a catheter 10, and FIG. 2 shows a partial cross-sectional view of the catheter 10.

As shown in FIG. 1, the catheter 10 comprises a catheter body 11, a flexible front end tip 12 attached to a front/distal end of the catheter body 11, and a connector 14 attached to a base/proximal end of the catheter body 11.

More specifically, the catheter body 11 comprises a hollow elongated member having a lumen 16 (FIG. 2) into which a guide wire may be inserted. In some embodiments, the full length of the catheter body 11 may be about 1500 mm. A front end part 18 of the catheter body 11 may extend for about 200 mm from the front/distal end of the catheter body 11 and may have an outer diameter of about 0.88 mm (0.85 to 0.90 mm) An intermediate part 20 of the catheter body 11 may extend from a base/proximal end of the front end part 18. The intermediate part 20 may extend for about 600 mm and may have an outer diameter slightly larger than that of the front end part 18. Further, a base end part 22 may extend from a base/proximal end of the intermediate part 20 to the connector 14. The base end part 22 may have an outer diameter even larger than that of the intermediate part 20. In other embodiments, the outer diameters of the front end part 18, the intermediate part 20, and the base end part 22 may be equal.

Moreover, as shown in FIG. 2, the catheter body 11 includes a hollow coil body 24, an inner resin layer 26 covering an inner periphery of the coil body 24, and an outer resin layer 28 covering an outer periphery of the coil body 24.

The inner resin layer 26 has a tube-like shape extending throughout the full length of the catheter body 11 along an innermost part of the catheter body 11. In addition, the lumen 16 of the catheter body 11 is formed in an inner cavity of the inner resin layer 26. Moreover, the inner resin layer 26 extends axially from the front/distal end of the catheter body 11 to a side of the catheter body 11 at the front/distal end.

The resin material of the inner resin layer 26 may be any conventional, well-known resin material as long as the resin material is sufficiently flexible with moderate plasticity. For example, the resin material may be polytetrafluoroethylene (PTFE), which has excellent lubricity, and is thus preferable in view of its slideability characteristics with a guide wire.

The coil body 24 is a hollow twisted wire coil in which two or more metal element wires 40, each having a circular cross section, are twisted (10 element wires in some embodiments). Further, because the coil body 24 is heat-treated by a well-known method, after the two or more element wires 40 are twisted, the residual stress of the coil body 24 is removed.

The metal material of the element wires 40 may be any conventional, well-known metal material. For example, metal materials such as stainless steel and/or a superelastic alloy such as a Ni—Ti may be used.

The outer resin layer 28, which constitutes the outermost layer of the catheter body 11, may extend the full length of the catheter body 11. Thus, the outer resin layer 28 may cover the entire outer periphery of the coil body 24 such that the entire outer periphery of the element wires 40 is not exposed.

A thickness of the outer resin layer 28 may be greater in the intermediate part 20 of the catheter body 11 than in the front end part 18 of the catheter body 11. Moreover, the thickness of the outer resin layer 28 may be greater in the base end part 22 of the catheter body 11 than in either the intermediate part 20 of the catheter body 11 or the front end part 18 of the catheter body 11. In other embodiments, the thickness of the outer resin layer 28 is equal in the front end part 18, the intermediate part 20, and the base end part 22.

Further, a hardness of the outer resin layer 28 may increase in incremental steps from the front end part 18 to the intermediate part 20 and from the intermediate part 20 to the base end part 22. Thus, the plasticity of the base end part 22, the intermediate part 20, and the front end part 18 increases from the base end part 22 to the front end part 18 in incremental steps.

The resin material of the outer resin layer 28 may be any conventional, well-known resin material as long as the resin material is sufficiently flexible with moderate plasticity. For example, the resin material may include polyamide elastomers and the like.

The front end tip 12 has an elongated tubular overall shape, and comprises a lumen communicating with the lumen 16 of the catheter body 11. Furthermore, the front end tip 12 may have a plasticity that is greater than that of the catheter body 11. In addition, the distal end of the front end tip 12 has a tapered outer periphery in which an outer diameter of the front end tip 12 gradually decreases toward a forefront part 48.

The material of the front end tip 12 may include any conventional and well-known resin material, as long as the resin material has a higher plasticity than that of the inner resin layer 26 and of the outer resin layer 28. For example, the material of the front end tip 28 may include polyurethane elastomers. In some embodiments, tungsten powder may be mixed into the material of the front end tip 12 in order to enhance visibility of the front end tip 12 under radioscopy.

As shown in FIG. 2, an inner periphery of the front end tip 12 includes the inner resin layer 26 extending from the front/distal end of the catheter body 11. Additionally, the front end tip 12 includes the coil body 24 extending from the front/distal end of the catheter body such that the coil body 24 is wound around and embedded around the outer periphery of the inner resin layer 26 in the front end tip 12. The coil body 24 may be disposed radially inward in the front end tip 12 such that the coil body 24 is closer to the inner periphery of the front end tip 12 than the outer periphery of the front end tip 12.

Moreover, the front end tip 12 may include a reinforcement body 30. As shown in FIG. 2, the reinforcement body 30 is fixed to the front end tip 12 and the coil body 24 in order to prevent detachment of the front end tip 12 from the coil body 24, even when the remainder of the front end tip 12 becomes detached from the remainder of the catheter body 11. Thus, the reinforcement body 30 prevents detachment of the front end tip 12 from the coil body 24, which in turn prevents detachment of the front end tip 12 from the catheter body 11. The reinforcement body 30 may include a resin material with a hardness greater than the resin material of the front end tip 12.

The material of the reinforcement body 30 may include, for example, polyamide elastomers. The polyamide elastomer of the reinforcement body 30 may be harder than the material of the outer resin layer 28.

Figure 3:
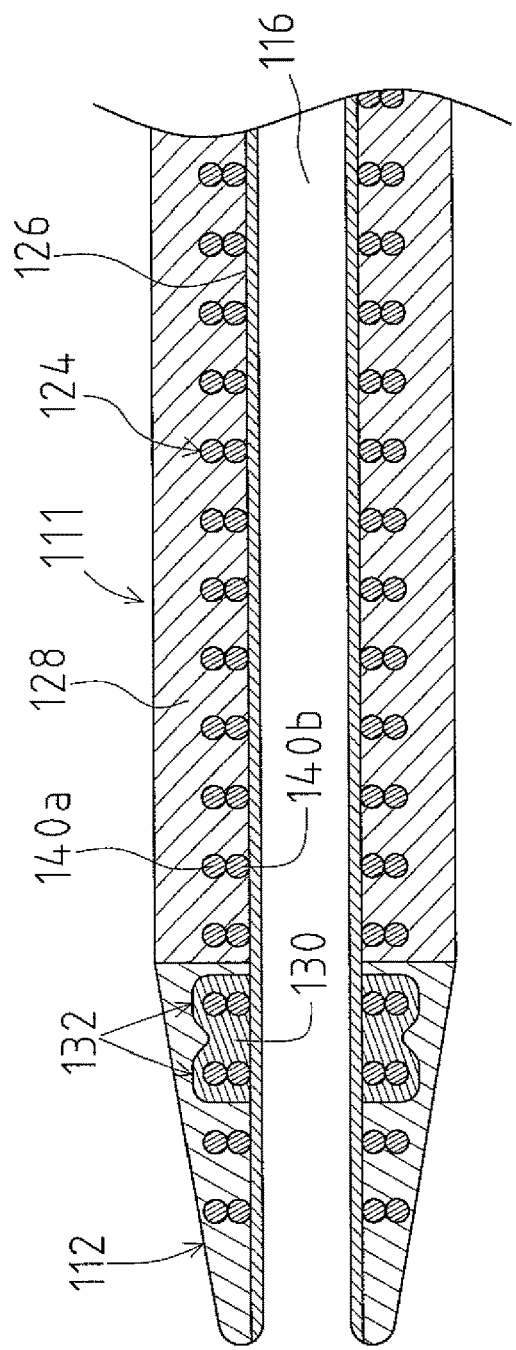
FIG. 3 shows a partial cross sectional view of the catheter according to embodiments.

The catheter according to the embodiment of FIG. 3 represents an embodiment in which the coil body 24 of the catheter according to the embodiment of FIG. 2 is replaced with a braid body 124. Further, since the catheter according to the embodiment of FIG. 3 has the same appearance as the catheter 10, only the internal structure is described with an overall view omitted.

As shown in FIG. 3, a catheter body 111 comprises a hollow elongated member having a lumen 116, into which a guide wire may be inserted. Similar to FIG. 2, the catheter body 111 has a braid body 124, an inner resin layer 126 covering the inner periphery of the braid body 124, and an outer resin layer 128 covering the outer periphery of the braid body 124.

The inner resin layer 126 has a tube-like shape extending throughout the full length of the catheter body 111 along an innermost part of the catheter body 111. Moreover, the inner resin layer 126 extends axially from a front/distal end of the catheter body 111 to a side of the catheter body 111 at the front/distal end. The material of the inner resin layer 126 may be similar to the material disclosed for the embodiment of FIG. 2.

The braid body 124 has a structure in which two metal element wires 140a and 140b are woven around each other in such a way to form a mesh-like structure. In addition, the braid body 124 is wound around an outer periphery of the inner resin layer 126 along the full length of the inner resin layer 126.

Further, the braid body 124 is wound around the outer periphery of the inner resin layer 126 such that both the braid body 124 and the inner resin layer 126 axially extend from the front/distal end of the catheter body 111 to a side of the catheter body 111 at the front/distal end. Additionally, the braid body 124 protrudes from the front/distal end of the catheter body 111 so that the braid body 124 extends into the front end tip 112.

The metal material of the element wires 140a and 140b may be any conventional, well-known metal material. For example, metal materials such as tungsten, stainless steel, and the like may be used. Tungsten may preferably be used in order to impart good visibility under radioscopy to the braid body 124. In embodiments, the element wires 140a and 140b may be made of the same or different materials.

There is no particular limitation for the size of the element wires 140a and 140b, but the size may be selected depending on the sizes (outer diameters) of the catheter body 111 and the front end tip 112 and the like. In some embodiments, the diameters of the element wires 140a and 140b are about 0.023 mm in diameter. It is also contemplated that element wires 140a and 140b may the same or of different sizes. Thus, for example, element wires 140a may have a larger diameter than element wires 140b.

The outer resin layer 128 constitutes the outermost layer of the catheter body 111. As shown in FIG. 3, the outer resin layer 128 extends the full length of the catheter body 111. Thus, the outer resin layer 128 may cover the entire outer periphery of the braid body 124 such that entire outer periphery of the element wires 140a and 140b is not exposed.

The material of the outer resin layer 128 may be similar to the material disclosed for the embodiment of FIG. 2.

The front end tip 112 has an elongated tubular overall shape, and comprises a lumen communicating with the lumen 116 of the catheter body 111. Furthermore, the front end tip 12 may have a plasticity that is greater than that of the catheter body 111. In addition, the distal end of the front end tip 112 has a tapered outer periphery in which the outer diameter of the front end tip gradually decreases toward a forefront part 48.

The material of the front end tip 112 may be similar to the material for the embodiment of FIG. 2.

As shown in FIG. 3, the inner periphery of the front end tip 112 includes the inner resin layer 126 extending from the front/distal end of the catheter body 111. Additionally, the front end tip 112 includes the braid body 124 extending from the front/distal end of the catheter body 111 such that the coil body 124 is wound around and embedded around the outer periphery of the inner resin layer 126 in the front end tip 112. The coil body 124 may be disposed radially inward in the front end tip 112 such that the coil body 124 is closer to the inner periphery of the front end tip 112 than the outer periphery of the front end tip 112.

Further, the front end tip 112 may include a reinforcement body 130. As shown in FIG. 3, the reinforcement body 130 is fixed to the front end tip 112 and the coil body 124 in order to prevent detachment of the front end tip from the braid body 124. Thus, the reinforcement body 130 prevents detachment of the front end tip 112 from the coil body 124, which in turn prevents detachment of the front end tip 112 from the catheter body 111. The reinforcement body 130 may include a resin material with a hardness greater than the resin material of the front end tip 112.

The reinforcement body 130 may have a length sufficient so that it is fixed to the front end tip 112 and to the coil body 124. As shown in FIG. 3, the reinforcement body 130 may include one or more protrusion parts 132 extending toward the outer periphery of the front end tip 112 in order to effectively prevent the detachment of the front end tip 112 from the catheter body 111 in the axial direction of the catheter. For example, the reinforcement body 130 may include two protrusion parts 32, as shown in FIG. 3. However, it is further contemplated that the reinforcement body 130 may include three or more protrusion parts 132.

Figure 4:
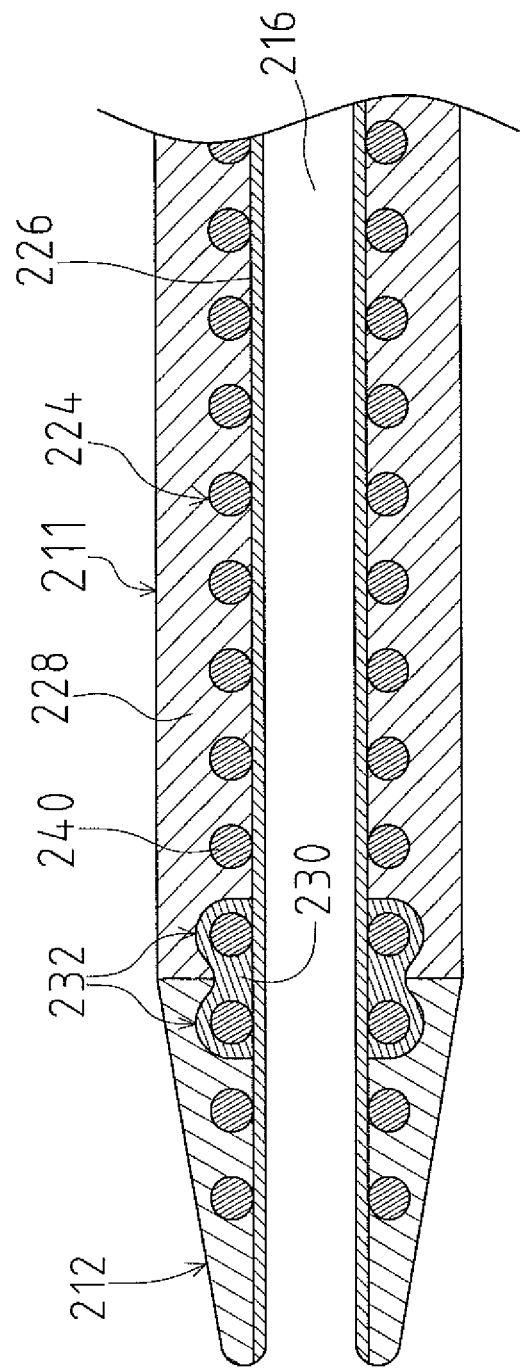
FIG. 4 shows a partial cross sectional view of the catheter according to embodiments.

The catheter according to the embodiment of FIG. 4 differs from the catheter according to the embodiment of FIG. 2 in that the position of the reinforcement body is different. That is, the reinforcement body of the catheter according to the embodiment of FIG. 4 is arranged in such a way to span the catheter body and the front end tip while the reinforcement body of the catheter according to the embodiment of FIG. 2 is arranged only within the front end tip.

Meanwhile, since the catheter according to the embodiment of FIG. 4 has the same appearance as the catheter 10, only the internal structure is described with an overall view omitted.

As shown in FIG. 4, a catheter body 211 comprises a hollow elongated member having a lumen 216 into which a guide wire may be inserted. The catheter body 211 has a coil body 224, an inner resin layer 226 covering the inner periphery of the coil body 224, and an outer resin layer 228 covering the outer periphery of the coil body 224.

The inner resin layer 226 has a tube-like shape extending throughout the full length of the catheter body 211 along an innermost part of the catheter body 211. Moreover, the inner resin layer 226 extends axially from the front/distal end of the catheter body 211 to a side of the catheter body 211 at the front/distal end. The material of the inner resin layer 226 may be similar to the material for the embodiments of FIGS. 2 and 3.

The coil body 224 is a hollow twisted wire coil in which two or more metal element wires 240, each having a circular cross section, are twisted (10 element wires in some embodiments). Further, because the coil body 224 is heat-treated by a well-known method, after the two or more element wires 240 are twisted, the residual stress of the coil body 224 is removed.

The material of the element wires may be similar to the material for the embodiments of FIGS. 2 and 3.

The outer resin layer 228 constitutes the outermost layer of the catheter body 211, which forms the outer surface of the catheter body 211. In addition, the outer resin layer 128 may extend the full length of the catheter body 211. Thus, the outer resin layer 128 may cover the entire outer periphery of the coil body 224 such that the entire outer periphery of the element wires 240 is not exposed.

The material of the outer resin layer 228 may be similar to the material for the embodiments of FIGS. 2 and 3.

Meanwhile, the front end tip 212 provided at the front/distal end of the catheter body 211 has an elongated tubular overall shape, and comprises a lumen communicating with the lumen 216 of the catheter body 211. Additionally, the front end tip 212 may have a plasticity greater than that of the catheter body 211. As shown in FIG. 4, the front end tip 212 has a tapered outer periphery in which the outer diameter of the front end tip 212 gradually decreases toward a forefront part 48.

The material of the front end tip 212 may be similar to the embodiments for FIGS. 2 and 3.

The inner periphery of the front end tip 212 includes the inner resin layer 226 extending from the front/distal end of the catheter body 211. Additionally, the front end tip 212 includes the coil body 224 extending from the front/distal end of the catheter body 211 such that the coil body 224 is wound around and embedded around the outer periphery of the inner resin layer 226 in the front end tip 212. The coil body 224 may be disposed radially inward in the front end tip 212 such that the coil body 224 is closer to the inner periphery of the front end tip 212 than the outer periphery of the front end tip 212.

Further, the front end tip 212 and catheter body 211 may include a reinforcement body 230 such that the reinforcement body 230 spans the catheter body 211 and the front end tip 212. As shown in FIG. 4, the reinforcement body 230 is fixed to the front/distal end part of the catheter body 211 and the base/proximal end part of the front end tip 212 in order to prevent detachment of the front end tip 212 from the catheter body 211. Furthermore, the reinforcement body 230 is fixed to the front end tip 212 and to the coil body 224 to prevent detachment of the front end tip 212 from the coil body 224. Thus, the reinforcement body 230 prevents detachment of the front end tip 212 from the coil body, which in turn prevents detachment of the front end tip 212 from the catheter body 211. The reinforcement body 230 may include a resin material with a hardness greater than the resin material of the front end tip 212

The reinforcement body 230 may have a length sufficient so that it is fixed to the front end tip 212 and to the coil body 224. As shown in FIG. 4, the reinforcement body 230 may include one or more protrusion parts 232 extending toward the outer periphery of the front end tip 212 in order to effectively prevent the detachment of the front end tip 212 from the catheter body 211 in the axial direction of the catheter. For example, the reinforcement body 230 may include two protrusion parts 232, as shown in FIG. 4. However, it is further contemplated that the reinforcement body 230 may include three or more protrusion parts 232.

Figure 5:
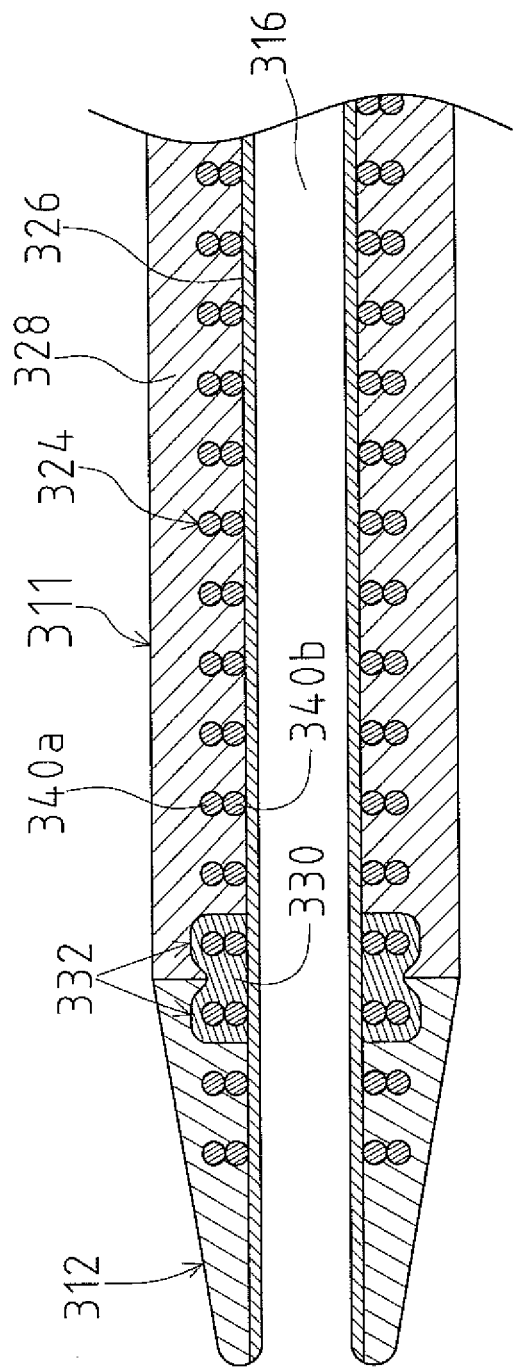
FIG. 5 shows a partial cross sectional view of the catheter according to embodiments.

The catheter according to the embodiment of FIG. 5 differs from the catheter according to the embodiment of FIG. 3 in that the position of the reinforcement body is different. That is, the reinforcement body of the catheter according to the embodiment of FIG. 5 is arranged in such a way to span the catheter body and the front end tip while the reinforcement body of the catheter according to the embodiment of FIG. 3 is arranged only within the front end tip. Further, since the catheter according to the embodiment of FIG. 5 also has the same appearance as the catheter 10, only the internal structure is described with an overall view omitted.

As shown in FIG. 5, a catheter body 311 comprises a hollow elongated member having a lumen 316 into which a guide wire may be inserted. The catheter body 311 has a braid body 324, an inner resin layer 326 covering the inner periphery of the braid body 324, and an outer resin layer 328 covering the outer periphery of the braid body 324.

The inner resin layer 326 has a tube-like shape extending throughout the full length of the catheter body 311 along an innermost part of the catheter body 311. Moreover, the inner resin layer 326 extends axially from the front/distal end of the catheter body 311 to a side of the catheter body 311 at the front/distal end. The material of the inner resin layer 326 may be similar to the material for the embodiments of FIGS. 2-4.

The braid body 324 has a structure in which two metal element wires 340a and 340b are woven around each other so as to form a mesh-like structure. In addition, the braid body 324 is wound around the outer periphery of the inner resin layer 326 along the full length of the inner resin layer 326.

Further, the braid body 324 is wound around the outer periphery of the inner resin layer 326 such that both the braid body 324 and the inner resin layer 326 axially extend from the front/distal end of the catheter body 311 to a side of the catheter body 311 at the front/distal end. Additionally, the braid body 324 protrudes from the front/distal end of the catheter body 311 so that the braid body 324 extends into the front end tip 312.

The material of the element wires 140a and 140b may be similar to the material for the embodiments of FIGS. 2-4.

The outer resin layer 328 comprises the outermost layer of the catheter body 311. In addition, the outer resin layer 328 may extend the full length of the catheter body 311. Thus, the outer resin layer 328 may cover the entire outer periphery of the braid body 324 such that the entire outer periphery of the element wires 340a and 340b is not exposed.

The material of the outer resin layer 328 may be similar to the material for the embodiments of FIGS. 2-4.

Further, the front end tip 312 has an elongated tubular overall shape, and comprises a lumen communicating with the lumen 316 of the catheter body 311. The front end tip 311 may have a plasticity that is greater than that of the catheter body 311. In addition, the distal end of the front end tip 312 has a tapered outer periphery in which the outer diameter gradually decreases toward a forefront part 48.

The material of the front end tip 312 may be similar to the material for the embodiments of FIGS. 2-4.

As shown in FIG. 5, the inner periphery of the front end tip 312 is includes the inner resin layer 326 extending from the front/distal end of the catheter body 311. Additionally, the front end tip 312 includes the braid body 324 extending from the front/distal end of the catheter body 311 such that the coil body 324 is wound around and embedded around the outer periphery of the inner resin layer 326 in the front end tip 312. The coil body 324 may be disposed radially inward in the front end tip 312 such that the coil body 324 is closer to the inner periphery of the front end tip 312 than the outer periphery of the front end tip 312.

Further, the front end tip 312 and the catheter body 311 may include a reinforcement body 330 such that the reinforcement body 330 spans the catheter body 311 and the front end tip 312. The reinforcement body 330 may be fixed to the front/distal end part of the catheter body 311 and to the base/proximal end part of the front end tip 312 in order to prevent detachment of the front end tip 312 from the catheter body 311. Furthermore, the reinforcement body 330 is fixed to the front end tip 312 and to the coil body 324 to prevent detachment of the front end tip 312 from the coil body 324, even when the remainder of the front end tip 312 becomes detached from the remainder of the catheter body 311. Thus, the reinforcement body 330 prevents detachment of the front end tip 311 from the coil body 324, which in turn prevents detachment of the front end tip 312 from the catheter body 311. The reinforcement body 330 may include a resin material with a hardness greater than the resin material of the front end tip 312.

The reinforcement body 330 may have a length sufficient so that it is fixed to the front end tip 312 and to the coil body 324. As shown in FIG. 5, the reinforcement body 130 may include one or more protrusion parts 332 extending toward the outer periphery of the front end tip 212 in order to effectively prevent the detachment of the front end tip 312 from the catheter body 311 in the axial direction of the catheter. For example, the reinforcement body 330 may include two protrusion parts 332, as shown in FIG. 5. However, it is further contemplated that the reinforcement body 330 may include three or more protrusion parts 132.

Figure 6:
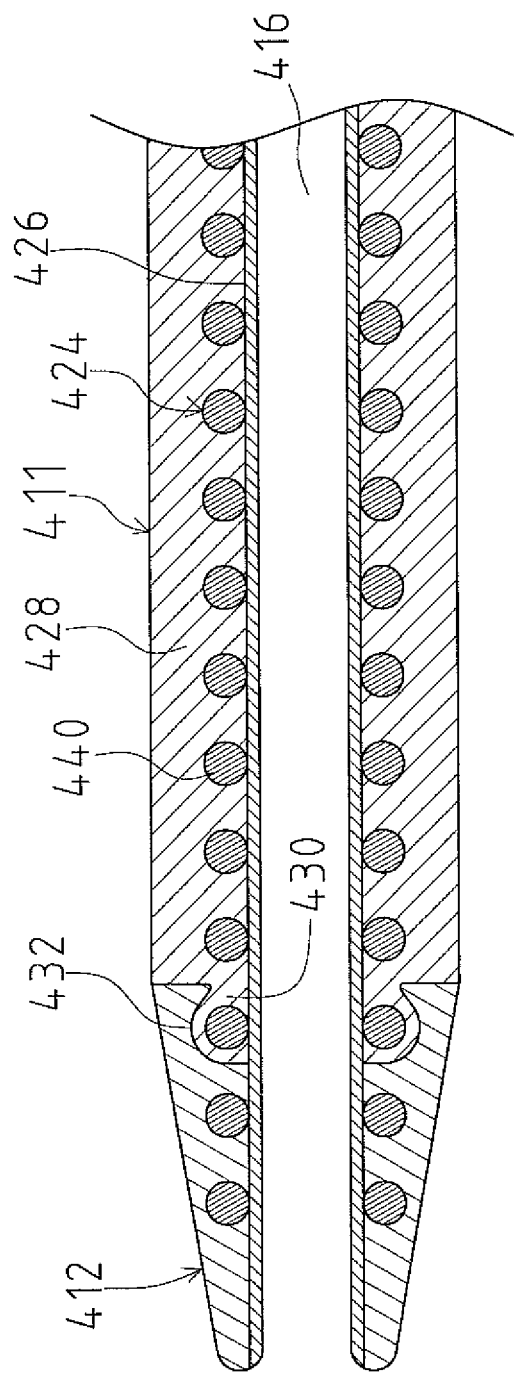
FIG. 6 shows a partial cross sectional view of the catheter according to embodiments.

The catheter according to the embodiment of FIG. 6 differs from the catheters according to the embodiments of FIGS. 2 and 3 in that the configuration of the reinforcement body is different. That is, the reinforcement body of the catheter according to the embodiment of FIG. 6 is integrally formed with the catheter body while the reinforcement bodies of the catheters according to the embodiments of FIGS. 2 and 3 are provided as separate bodies from the catheter bodies.

Note that since the catheter according to the embodiment of FIG. 6 has the same appearance as the catheter 10, the internal structure is described with an overall view omitted.

As shown in FIG. 6, a catheter body 411 comprises a hollow elongated member having a lumen 416 into which a guide wire may be inserted. The catheter body 411 has a coil body 424, an inner resin layer 426 covering the inner periphery of the coil body 424, and an outer resin layer 428 covering the outer periphery of the coil body 424.

The inner resin layer 426 has a tube-like shape extending throughout the full length of the catheter body 411 along an innermost part of the catheter body 411. Moreover, the inner resin layer 426 extends axially from the front/distal end of the catheter body 411 to a side of the catheter body 411 at the font/distal end. The material of the inner resin layer 426 may be similar to the material for the embodiments of FIGS. 2-5.

The coil body 424 is a hollow twisted wire coil in which two or more metal element wires 440, each having a circular cross section, are twisted (10 element wires in some embodiments). Further, because the coil body 424 is heat-treated by a well-known method, after the two or more metal element wires 440 are twisted, the residual stress of the coil body 424 is removed.

The material of the element wire 40 may be similar to the material for the embodiments of FIGS. 2-6.

The outer resin layer 428 constitutes the outermost layer which forms the outer surface of the catheter body 411. In addition, the outer resin layer 428 may extend the full length of the catheter body 411. Thus, the outer resin layer 428 may cover the entire outer periphery of the coil body 424 such that the entire outer periphery of the element wires 440 is not exposed.

The material of the outer resin layer 428 may be similar to the material for the embodiments of FIGS. 2-5.

Meanwhile, the front end tip 412 has an elongated tubular overall shape, and comprises a lumen communicating with the lumen 416 of the catheter body 411. The front end tip 412 may have a plasticity that is greater than that of the catheter body 411. In addition, the distal end of the front end tip 412 has a tapered outer periphery in which the outer diameter gradually decreases toward a forefront part 48.

The material of the front end tip 412 may be similar to the material for the embodiments of FIGS. 2-5.

As shown in FIG. 6, the inner periphery of the front end tip 412 includes the inner resin layer 426 extending from the front/distal end of the catheter body 411. Additionally, the front end tip 412 includes the coil body 424 extending from the front/distal end of the catheter body 411 such that the coil body 424 is wound around and embedded around the outer periphery of the inner resin layer 426 in the front end tip 412. The coil body 424 may be disposed radially inward in the front end tip 412 such that the coil body 424 is closer to the inner periphery of the front end tip 412 than the outer periphery of the front end tip 412.

Moreover, the front end tip 412 may include a reinforcement body 430 that extends from the front/distal end of the catheter body 411. As shown in FIG. 6, the reinforcement body 430 may be integrally formed with the catheter body 411 and extend into the front end tip 412. The reinforcement body 430 may be fixed to the base/proximal end part of the front end tip 412 in order to prevent detachment of the front end tip 412 from the catheter body 411. Additionally, the reinforcement body 430 may be fixed to front end tip 412 and to the coil body 424 in order to prevent detachment of the front end tip 412 from the coil body 424.

Here, the reinforcement body 430 may have a length sufficient so that it is fixed to the front end tip 412 and to the coil body 424. As shown in FIG. 6, the reinforcement body 430 may include one or more protrusion parts 432 extending toward the outer periphery of the front end tip 412 in order to effectively prevent the detachment of the front end tip 412 from the catheter body 411 in the axial direction of the catheter.

Although FIG. 6 shows one protrusion part 432, it is further contemplated that the reinforcement body 430 may include two, three, etc. protrusion parts 432.

Figure 7:
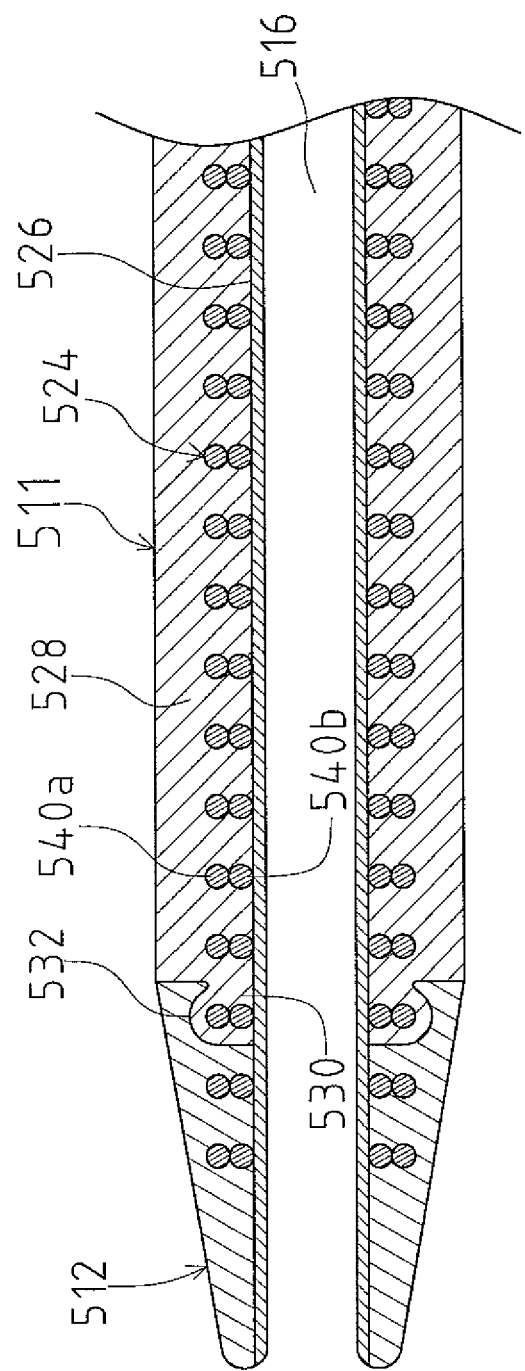
FIG. 7 shows a partial cross sectional view of the catheter according to embodiments.

The catheter according to the embodiment of FIG. 7 differs from the catheters according to the embodiments of FIGS. 3 and 5 in that the configuration of the reinforcement body is different. That is, the reinforcement body of the catheter according to the embodiment of FIG. 7 is integrally formed with the catheter body while the reinforcement bodies of the catheters according to the embodiments of FIGS. 3 and 5 are provided as separate bodies from the catheter bodies.

Note that since the catheter according to the embodiment of FIG. 7 has the same appearance as the catheter 10, only the internal structure is described with an overall view omitted.

As shown in FIG. 7, a catheter body 511 comprises a hollow elongated member having a lumen 516 into which a guide wire may be inserted. The catheter body 511 has a braid body 524, an inner resin layer 526 covering the inner periphery of the braid body 524, and an outer resin layer 528 covering the outer periphery of the braid body 524.

The inner resin layer 526 has a tube-like shape extending throughout the full length of the catheter body 511 along an innermost part of the catheter body 511. Moreover, the inner resin layer 526 extends axially from the front/distal end of the catheter body 511 to a side of the catheter body 511 at the front/distal end. The material of the inner resin layer 526 may be similar to the material for the embodiments of FIGS. 2-6.

The braid body 524 has a structure in which two metal element wires 540a and 540b are woven around each other so as to form a mesh-like structure. In addition, the braid body 524 is wound around the outer periphery of the inner resin layer 526 along the full length of the inner resin layer 526.

Further, the braid body 524 is wound around the outer periphery of the inner resin layer 526 such that both the braid body 524 and the inner resin layer 526 axially extend from the front/distal end of the catheter body 511 to a side of the catheter body 511 at the front/distal end. Additionally, the braid body 524 protrudes from the front/distal end of the catheter body 511 so that the braid body 524 extends into the front end tip 512.

The material of the element wires 140a and 140b may be similar to the material for the embodiments of FIGS. 2-6.

The outer resin layer 528 constitutes the outermost layer which forms the outer surface of the catheter body 511. In addition, the outer resin layer 528 may extend the full length of the catheter body 511. Thus, the outer resin layer 528 may cover the entire outer periphery of the braid body 524 such that the entire outer periphery of the element wires 540a and 540b is not exposed.

The material of the outer resin layer 528 may be similar to the material for the embodiments of FIGS. 2-6.

Meanwhile, the front end tip 512 has an elongated tubular overall shape, and comprises a lumen communicating with the lumen 516 of the catheter body 511. Furthermore, the front end tip 512 may have a plasticity that is greater than that of the catheter body 511. In addition, the distal end of the front end tip 512 has a tapered outer periphery in which the outer diameter of the front end tip gradually decreases toward a forefront part 48.

The material of the front end tip 512 may be similar to the material for the embodiments of FIGS. 2-6.

As shown in FIG. 7, the inner periphery of the front end tip 512 includes the inner resin layer 526 extending from the front/distal end of the catheter body 511. Additionally, the front end tip 512 includes the braid body 524 extending from the front/distal end of the catheter body 511 such that the coil body 524 is wound around and embedded around the outer periphery of the inner resin layer 526 in the front end tip 512. The coil body 524 may be disposed radially inward in the front end tip 512 such that the coil body 524 is closer to the inner periphery of the front end tip 512 than the outer periphery of the front end tip 512.

Moreover, the front end tip 512 may include a reinforcement body 530. As shown in FIG. 7, the reinforcement body 530 extends from the front/distal end of the catheter body 511 and is fixed to the base/proximal end part of the front end tip 512. Thus, detachment of the front end tip 512 from the catheter body 511 can be prevented.

The reinforcement body 530 may have a length sufficient so that it is fixed to the front end tip 512 and to the braid body 524. As shown in FIG. 7, the reinforcement body 530 may include one or more protrusion parts 532 extending toward the outer periphery of the front end tip 512 in order to effectively prevent the detachment of the front end tip 512 from the catheter body 511 in the axial direction of the catheter.

The reinforcement body5 530 may include two, three, or more protrusion parts 532.

The present disclosure shall not be limited by the examples and embodiments disclosed herein.

For example, in the embodiments described above, all the reinforcement bodies are each illustrated to have a larger diameter than the coil body or the braid body, but the reinforcement body does not necessarily have a lager diameter than the coil body or the braid body.

Further, in the aforementioned embodiments, the reinforcement body is described to comprise a resin material that is harder than that of the front end tip, but the reinforcement body does not necessarily comprise a resin material that is harder than that of the front end tip.

Moreover, the coil body in the aforementioned embodiments comprises 10 metal element wires, each having the same diameter. However, the coil body, for example, may comprise 10 metal element wires such that 8 wires have the same diameter and 2 wires have a different diameter. Alternatively, the coil body may include only a single metal element wire.

Two or more element wires are preferably used to form the coil body in order to reduce elongation of the coil body.

Moreover, for the coil body in the aforementioned embodiments, each metal element wire constituting the coil body is arranged in such a way to be spaced in the axial direction of the catheter body, forming a sparsely wound state. Nonetheless, in a case where enhanced stiffness of the catheter is preferred, or enhanced torque transmittability from the base/proximal end of the catheter to the front/distal end is preferred, a densely wound sate is preferred in which each element wire is arranged in such a way to make contact with each other.

Further, the braid body in the aforementioned embodiments is formed with two inter-woven element wires having the same diameter, but it may be formed with a braid body comprising element wires having different diameters. Further the braid body may be formed not only with two inter-woven element wires but also with more than two inter-woven element wires, and may be formed with clockwise element wires and counter-clockwise element wires, the number of the clockwise element wires and the counter-clockwise element wires being different.

Moreover, the element wires constituting the braid body in the aforementioned embodiments are metal element wires, but the braid body may be formed with woven resin element wires, or may be formed with a metal element wire and a resin element wire woven with each other in combination. Furthermore, the number of element wires and the braiding manner of element wires to form a braid body may appropriately be altered.

Further, the element wire which constitutes the coil body and the braid body in the aforementioned embodiments has a circular cross section, but the coil body and the braid body may be formed with an element wire with an elliptical cross section or an element wire with a rectangular cross section.

Moreover, the protrusion part in the aforementioned embodiments is described to have a curved shape on the whole, but is not limited to this shape. For example, the protrusion part may have a sharply pointed shape on the front end tip, or may enter into the front end tip in a wedge-like manner.

Furthermore, in the aforementioned embodiments, the coil body or the braid is arranged at the outer periphery of the inner resin layer so that the coil body and the braid may easily be formed. Nonetheless, the inner resin layer may be integrally formed with the outer resin layer, and then a coil body or a braid may be arranged in the inside of an additional resin layer. Further, in addition to the two-layered structure of an inner resin layer and an outer resin layer, a configuration in which a coil body or a braid is arranged in a certain layer of a multilayered structure having three or more layers may be used.

Moreover, a configuration in which a coil body alone or a braid alone is arranged in each catheter is described in the aforementioned embodiments, but even a configuration in which a coil body and a braid are both arranged in one catheter may be used.

The invention claimed is:

1. A catheter comprising:
    a catheter body having a distal end and a proximal end and forming a lumen,
    a resin front end tip having a lumen in communication with the lumen of the catheter body, the front end tip being attached to the distal end of the catheter body,
    a wound body disposed in the catheter body and in the front end tip such that the wound body extends along the lumen of the catheter body, the wound body being a coil and/or a braid, and
    a resin reinforcement body disposed at least partly within the front end tip, the resin reinforcement body radially covering the wound body such that the wound body is embedded in the resin reinforcement body, and the resin reinforcement body including a plurality of protrusions extending toward an outer periphery of the front end tip.

2. The catheter according to claim 1, wherein the resin reinforcement body has a diameter larger than a diameter of the wound body.

3. The catheter according to claim 2, wherein the resin reinforcement body, including the plurality of protrusions, spans the catheter body and the front end tip such that the resin reinforcement body is disposed on both the catheter body and the front end tip.

4. The catheter according to claim 2, wherein the resin reinforcement body is integrally formed with the catheter body.

5. The catheter according to claim 2, wherein an entirety of the resin reinforcement body is disposed entirely within the front end tip.

6. The catheter according to claim 2, further comprising an inner resin layer, wherein the wound body and the resin reinforcement body are disposed radially outward of the inner resin layer.

7. The catheter according to claim 1, wherein the resin reinforcement body, including the plurality of protrusions, spans the catheter body and the front end tip such that the resin reinforcement body is disposed on both the catheter body and the front end tip.

8. The catheter according to claim 1, wherein the resin reinforcement body is integrally formed with the catheter body.

9. The catheter according to claim 1, wherein an entirety of the resin reinforcement body is disposed entirely within the front end tip.

10. The catheter according to claim 1, further comprising an inner resin layer, wherein the wound body and the resin reinforcement body are disposed radially outward of the inner resin layer.

* * * * *